US008680844B2

United States Patent
Burnett et al.

(10) Patent No.: US 8,680,844 B2
(45) Date of Patent: Mar. 25, 2014

(54) FORCE COMPENSATED PROBE

(75) Inventors: Philip Frank Burnett, Niskayuna, NY (US); Daniel Lawrence Banowetz, Glenville, NY (US); Lisa Ann Hong, Schenectady, NY (US)

(73) Assignee: General Electric Company, Schenectady, NY (US)

( * ) Notice: Subject to any disclaimer, the term of this patent is extended or adjusted under 35 U.S.C. 154(b) by 577 days.

(21) Appl. No.: 12/957,798

(22) Filed: Dec. 1, 2010

(65) Prior Publication Data

US 2012/0139528 A1    Jun. 7, 2012

(51) Int. Cl.
*G01R 1/06*     (2006.01)
*G01N 27/04*    (2006.01)
*G01R 1/067*    (2006.01)

(52) U.S. Cl.
CPC ............. *G01N 27/04* (2013.01); *G01N 27/045* (2013.01); *G01N 27/048* (2013.01); *G01R 1/067* (2013.01); *G01R 1/06788* (2013.01)
USPC .. 324/147; 324/551; 324/754.02; 324/754.03

(58) Field of Classification Search
CPC .... G01R 1/067; G01R 6/722; G01R 1/06738; G01R 1/06788; G01N 27/04; G01N 27/041; G01N 27/045; G01N 27/048
USPC ................... 73/73–77; 324/149, 551, 754.03, 324/754.13, 755.07–755.09, 755.11
See application file for complete search history.

(56) References Cited

U.S. PATENT DOCUMENTS

| 2,582,629 | A  | * | 1/1952  | Hilton ........................ 324/696 |
| 6,114,863 | A  | * | 9/2000  | Krahn et al. ................ 324/664 |
| 6,370,426 | B1 |   | 4/2002  | Campbell et al. |
| 6,434,851 | B1 | * | 8/2002  | Nishina ......................... 33/559 |
| 6,906,530 | B2 | * | 6/2005  | Geisel .......................... 324/664 |
| 7,087,019 | B2 | * | 8/2006  | Kao ............................ 600/306 |
| 2006/0267602 | A1 | * | 11/2006 | Yang et al. .................. 324/754 |
| 2006/0290362 | A1 | * | 12/2006 | Prey et al. ................... 324/754 |
| 2007/0179353 | A1 | * | 8/2007  | Fraden ........................ 600/300 |
| 2010/0089187 | A1 | * | 4/2010  | Yin et al. ..................... 73/866.5 |
| 2010/0109651 | A1 | * | 5/2010  | Tolmachev et al. ......... 324/149 |
| 2010/0162812 | A1 | * | 7/2010  | Parkinson ..................... 73/299 |

FOREIGN PATENT DOCUMENTS

DE      29 12 349 A1    10/1980
JP      2008008659 A  *  1/2008

OTHER PUBLICATIONS

Search Report issued in connection with GB Patent Application No. 1120251.2, Mar. 23, 2012.

* cited by examiner

*Primary Examiner* — Jeff Natalini
*Assistant Examiner* — Adam Clarke
(74) *Attorney, Agent, or Firm* — Cantor Colburn LLP

(57) ABSTRACT

A force compensated probe for electrical measurement is provided and includes a support structure having a back plate and sidewalls, a probe for electrical measurement of an article and an elastic base disposed to supportively couple the probe to the back plate such that the probe normally protrudes away from the back plate beyond distal edges of the sidewalls, and, when the probe is applied to the article for the electrical measurement such that components of the support structure contact the article, a predefined load is consistently applied to the elastic base.

19 Claims, 6 Drawing Sheets

US 8,680,844 B2

FORCE COMPENSATED PROBE

BACKGROUND OF THE INVENTION

The subject matter disclosed herein relates to a force compensated probe for measurement of an electrical property of an article.

For electrical generators, the generator armature is provided with electrical insulation to protect the generator components from electrical faults. This insulation performs most efficiently when it is in good condition but tends to degrade when it is moist or when it is exposed to moisture. It is therefore helpful to determine when such moisture is present so that repair can be conducted or planned.

Determining when moisture is present may involve the measurement of the electrical impedance of the insulation. Typically, the insulation has characteristic electrical impedance when it is dry but decreased impedance when moist. As such, one can determine when moisture is present by determining the electrical impedance of the insulation and comparing that impedance with the characteristic impedance for dry insulation. Unfortunately, the tools for measuring electrical impedance are also sensitive to an amount of mechanical force applied by the tools to the insulation being tested so the readings have often been inconsistent.

Efforts to mitigate the problems associated with the sensitivity of tools for measuring electrical impedance have involved the use of audio and/or visual feedback mechanisms referred to as "contact factor" mechanisms in attempts to provide consistent readings. These contact factor mechanisms do not, however, limit an amount of force that can be applied by the operator and are, therefore, subject to operator error.

BRIEF DESCRIPTION OF THE INVENTION

According to one aspect of the invention, a force compensated probe for electrical measurement is provided and includes a support structure having a back plate and sidewalls, a probe for electrical measurement of an article and an elastic base disposed to supportively couple the probe to the back plate such that the probe normally protrudes away from the back plate beyond distal edges of the sidewalls, and, when the probe is applied to the article for the electrical measurement such that components of the support structure contact the article, a predefined load is consistently applied to the elastic base.

According to another aspect of the invention, a force compensated probe for electrical measurement is provided and includes an enclosure having a back plate and sidewalls extending around the back plate to form an enclosure defined from the back plate to distal edges of the sidewalls, a probe for electrical measurement of an article and an elastic base disposed within the enclosure to supportively couple the probe to the back plate such that the probe normally protrudes away from the back plate beyond the sidewall distal edges, and, when the enclosure and the probe are applied to the article for the electrical measurement, a predefined load is consistently applied to the elastic base.

According to yet another aspect of the invention, a force compensated probe for electrical measurement is provided and includes an enclosure having a back plate and sidewalls extending around the back plate to form an enclosure with a depth defined from a plane of the back plate to a plane cooperatively defined by distal edges of the sidewalls, a protectively covered probe for measurement of electrical impedance of an article and an elastic base disposed within the enclosure to supportively couple the probe to the back plate such that the probe normally protrudes away from the back plate beyond the sidewall distal edges, and, when the enclosure and the probe are applied to the article for the electrical measurement, a combined height of the probe and the elastic base from the plane of the back plate is substantially similar to the enclosure depth with a predefined load thereby consistently applied to the elastic base irrespective of increases in application forces.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

Figure 1:
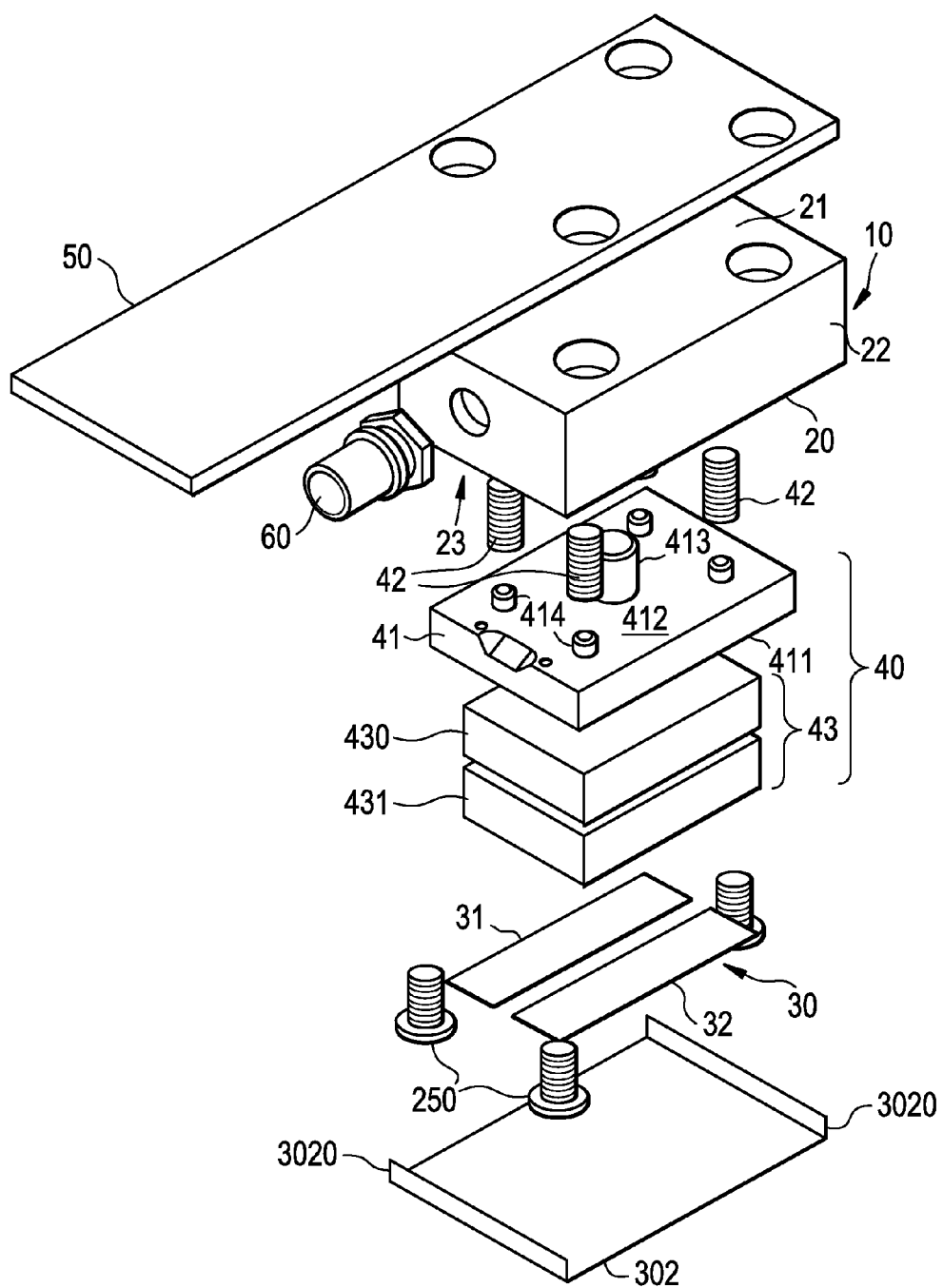
FIG. 1 is an exploded perspective view of a force compensated probe.
Figure 2:
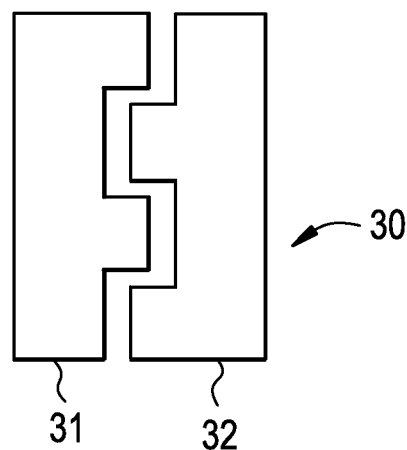
FIG. 2 is a view of an exemplary probe according to alternative embodiments.

The detailed description explains embodiments of the invention, together with advantages and features, by way of example with reference to the drawings.

DETAILED DESCRIPTION OF THE INVENTION

With reference to FIGS. 1-5, a force compensated probe 10 for electrical measurement of, for example, an electrical impedance of a dry, moist or wet article is provided. The force compensated probe 10 includes an enclosure 20, a probe 30 and an elastic base 40. The enclosure 20 has a substantially planar back plate 21 and sidewalls 22 that extend around a rim of the back plate 21 to form an enclosure 23, which may be rectangular and/or rectangular with curved corners. This enclosure 23 has a depth, D, as defined from a plane of the back plate 21 to a plane cooperatively defined by distal edges 24 of the sidewalls 22.

Screws having screw heads 250 may be additionally installed into the sidewalls 22 such that summits of the screw heads 250 cooperatively define the distal edges 24 and establish a substantially uniform height, H, of the sidewalls 22 as well as the depth, D. The screws may be arrayed around the sidewalls 22 in various configurations. For example, two screws may be arrayed at opposite ends of a first one of the sidewalls 22 and a third screw may be arrayed at a mid-point of a second one of the sidewalls 22, which is opposite the first one of the sidewalls 22 to thereby form a triangular arrangement. For purposes of clarity and brevity, configurations of the enclosure 20 with the screws installed in the sidewalls 22 will be employed for descriptive purposes below.

The force compensated probe 10 further includes a handle 50 and an electrical connector 60. The handle 50 may be attached or fastened to the enclosure 20 or, more particularly, to the back plate 21 and provides a grip surface to an operator that facilitates application of the force compensated probe 10 to the article. The electrical connector 60 is electrically coupled to the probe 30 via a through-hole defined in one or more of the sidewalls 22. The electrical connector 60 may be any type of electrical connector having two or more distinct conductive elements.

The probe 30 is configured for measurement of an electrical property of the article. In accordance with embodiments, the probe 30 measures electrical impedance of the article where the article includes insulation of a generator armature bar that tends to become and/or risks becoming moist over time. This moisture leads to a deterioration in performance capability of the insulation and is identifiable in accordance with impedance levels. Thus, by measuring the electrical impedance of the insulation, it can be determined whether the moisture content of the insulation is within established parameters or excessive.

Figure 3:
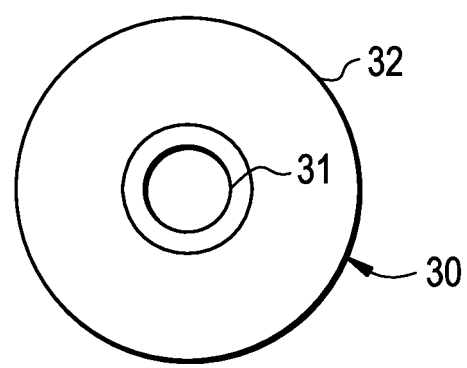
FIG. 3 is a view of an exemplary probe according to alternative embodiments.

The probe 30 may be formed of copper, a copper alloy or some other similar metallic or metallic alloy and may include, for example, parallel metallic strips 31, 32 that are electrically isolated from one another, substantially parallel metallic strips having labyrinthine adjacent edges (see FIG. 2) that are electrically isolated from one another and/or metallic members surrounding but electrically isolated from another metallic member (see FIG. 3). A choice of probe 30 configurations or designs can be based on various factors including, but not limited, to cost and the type, shape and/or size of the article to be measured and a degree of measurement sensitivity desired/required. For example, a relatively small or curved article surface would call for a small probe 30 configuration (i.e., one conductor surrounding another) that can be applied with relatively precise positioning whereas a relatively large article surface may call for a larger probe 30 configuration (i.e., parallel strips). Similarly, a requirement for a highly sensitive measurement would call for a relatively large sized probe 30, if space constraints permit.

The elastic base 40 is disposed within the enclosure 20 to supportively couple the probe 30 to the back plate 21 such that the probe 30 normally protrudes away from the back plate 21 beyond the distal edges 24 of the sidewalls 22, and, when the enclosure 20 is applied to the article for the electrical measurement in a manner as will be described below, a combined height of the probe 30 and the elastic base 40 as measured from the plane of the back plate 21 is substantially similar to the enclosure 20 depth, D. Thus, a predefined load is consistently applied to the elastic base 40. That is, when the operator applies the force compensated probe 10 to the article, the operator initially feels the loading of the elastic base 40 as the press force applied to the probe 30 onto the article increases. As the application continues, however, the summits of the screw heads 250, which establish the plane of the distal edges 24 of the sidewalls 22, come into contact with the article and the operator is prevented from applying any additional pressing forces to the probe 30 as the force will not be transferred through the screws directly to the article. At this point, in accordance with embodiments, the pre-loading of the elastic base 40 may be equivalent to about a ⅛ inch (0.3 cm) elastic base 40 deformation. From this point forward, even as the operator may continue to increase a press force of the force compensated probe 10 onto the article, the operator is prevented from increasing the pressing force of the probe 30 onto the article.

As such, the probe 30 is pressed onto the article with consistent force irrespective of the pressing force applied by the operator and data produced by the measurements conducted by the probe 30 are unaffected by human error associated with uneven press forces. Thus, an accuracy of the measurements of, for example, the electrical impedance of the insulation may be increased and an accuracy of the determinations of whether the moisture content of the insulation is within established parameters or excessive can also be increased.

Figure 4:
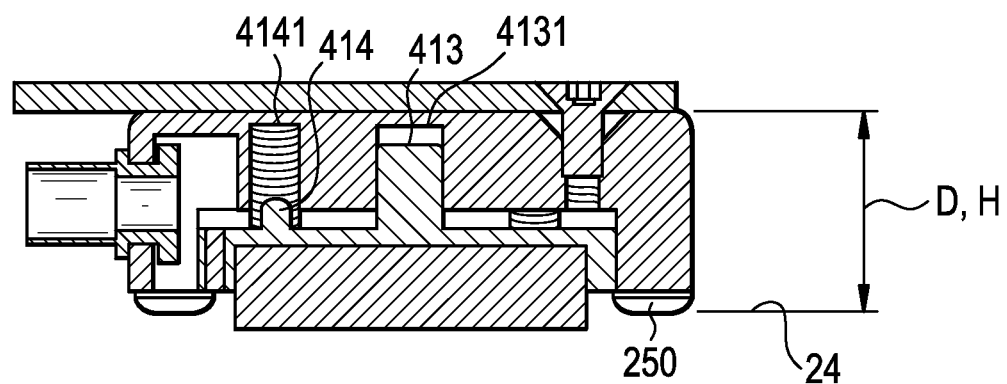
FIG. 4 is a side sectional view of the force compensated probe of FIG. 1.

As shown in FIGS. 1 and 4, the elastic base 40 may include a guide plate 41, elastic elements 42 and an insulating element 43. The guide plate 41 has a generally planar body and front and back faces 411 and 412, respectively, and further includes a protrusion 413 and bosses 414. The protrusion 413 is extendable from the back face 412 and through a guide slot 4131 formed through the back plate 21 to constrain movement of the guide plate 41 associated with loading and unloading of the elastic base 40. The bosses 414 also extend from the back face 412 and may be arrayed about the protrusion 413. The elastic elements 42 are supportively interposed between the guide plate 41 and the back plate 21 and may include, for example, compressive springs that are each anchored to the bosses 414, are each extendable into recesses 4141 defined in the back plate 21 and are each arranged such that the guide plate 41 is biased to remain substantially parallel with the back plate 21. In this way, with the front and back faces 411 and 412 substantially parallel with one another, the probe 30 can always be presented to the article with a consistent orientation at least with respect to the back plate 21. In accordance with alternate embodiments, the elastic elements 42 may be formed of a foam layer having a consistent spring constant. The insulating element 43 is supportively and electrically interposed between the guide plate 41 and the probe 30 and may include a first layer 430 of, for example, foam rubber and a second layer 431 of, for example, a dielectric material. The first layer 430 serves to encourage the probe 30 to conform in shape to that of the article and, in accordance with some embodiments, the dielectric material may include polyethylene foil that can keep the first layer 430 relatively dry.

Figure 6:
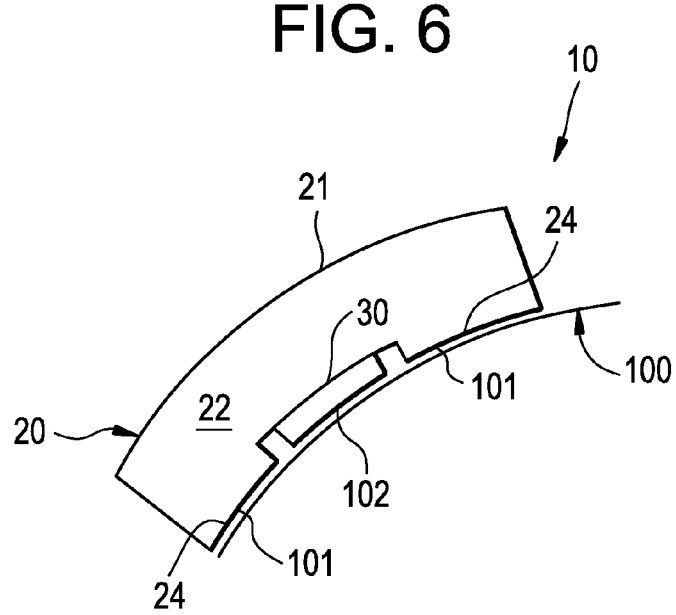
FIG. 6 is a side view of a force compensated probe in accordance with further embodiments.

In accordance with further embodiments and, with reference to FIG. 6, it is to be understood that the sidewalls 22, the distal edges 24 and the probe 30 need not be flat as long as the probe 30 can be presented to the article consistently with force compensation as described above. Indeed, for an article having a curved surface 100 or an otherwise uneven surface, the distal edges 24 and the probe 30 may be provided with similarly curved surfaces 101, 102, respectively, or similarly uneven surfaces such that they can be form fit to the curvature of the curved surface 100.

Figure 7A:
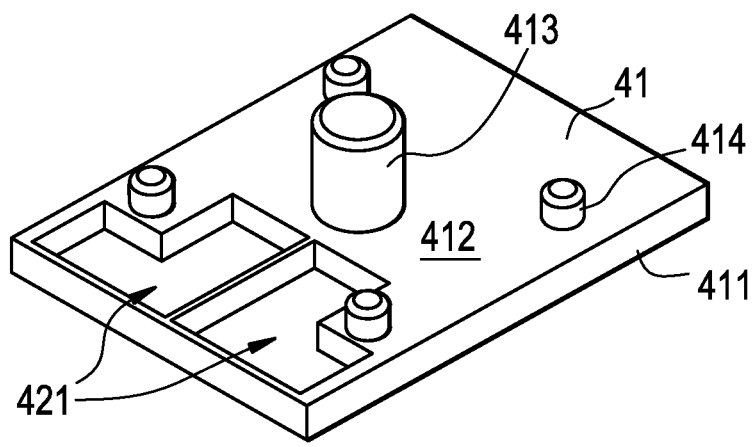
FIGS. 7A and 7B are opposite perspective views of a guide plate according to alternate embodiments of the invention.
Figure 7B:
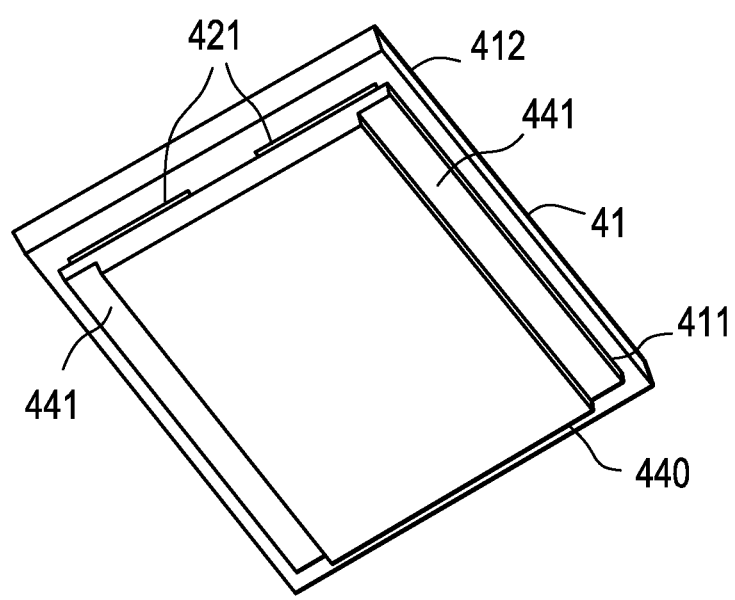
Figure 8:
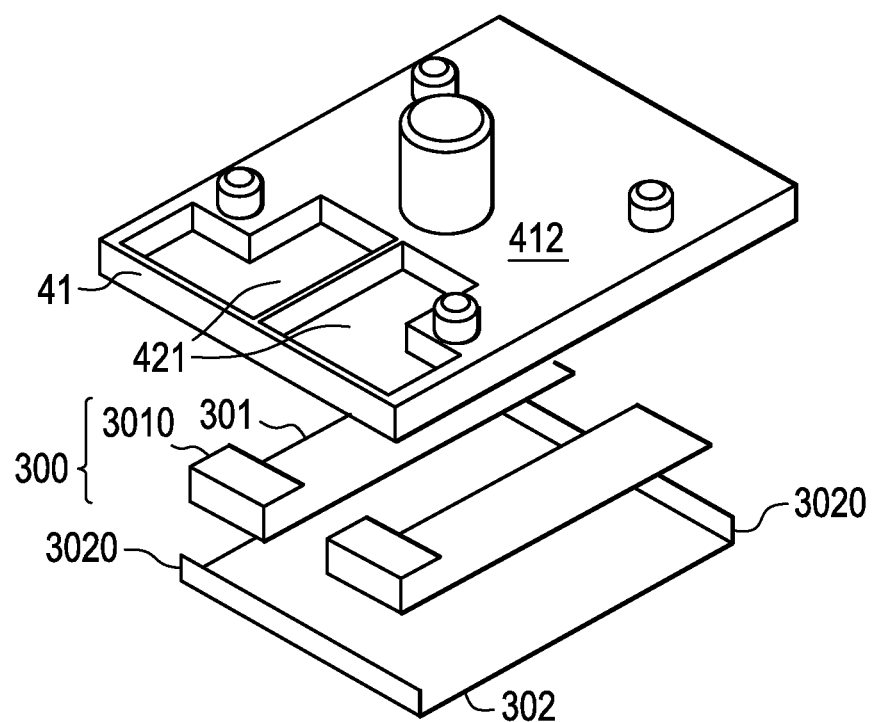
FIG. 8 is an exploded perspective view of components of a probe including the guide plate of FIGS. 7A and 7B.

With reference to FIGS. 7A, 7B and 8, alternate embodiments of the guide plate 41 are illustrated. In accordance with these alternate embodiments, the guide plate 41 includes the protrusion 413 and the bosses 414, as described above. In addition, the first and second layers 430 and 431 may be discarded, the guide plate 41 is formed to define cavities 421 and the guide plate 41 includes a secondary plate 440 with step formations 441. As shown in FIG. 8, an alternate probe 300 includes copper strips 301, which are formed similarly as described above, and which are further formed to include hook portions 3010. The copper strips 301 are supported on the secondary plate 440 with the hook portions 3010 extending about an edge of the secondary plate 440. Ends of the hook portions 3010 have respective exposed sections that are exposed through the cavities 421 for contact or another type of electrical communication with, for example, the electrical connector 60.

In operation, as the alternate probe 300 is applied to an article, the elastic elements 42 are compressed and the guide plate 41 moves toward the back plate 21. Concurrently, the respective exposed sections of the hook portions 3010 move through the cavities 421 toward the electrical connector 60. Once the enclosure 20 is applied to the article as described above such that the operator is prevented from applying any additional pressing forces, the respective exposed sections of the hook portions 3010 either contact the electrical connector 60 or are disposed close enough to provide for another type of electrical communication with the electrical connector 60.

Figure 5:
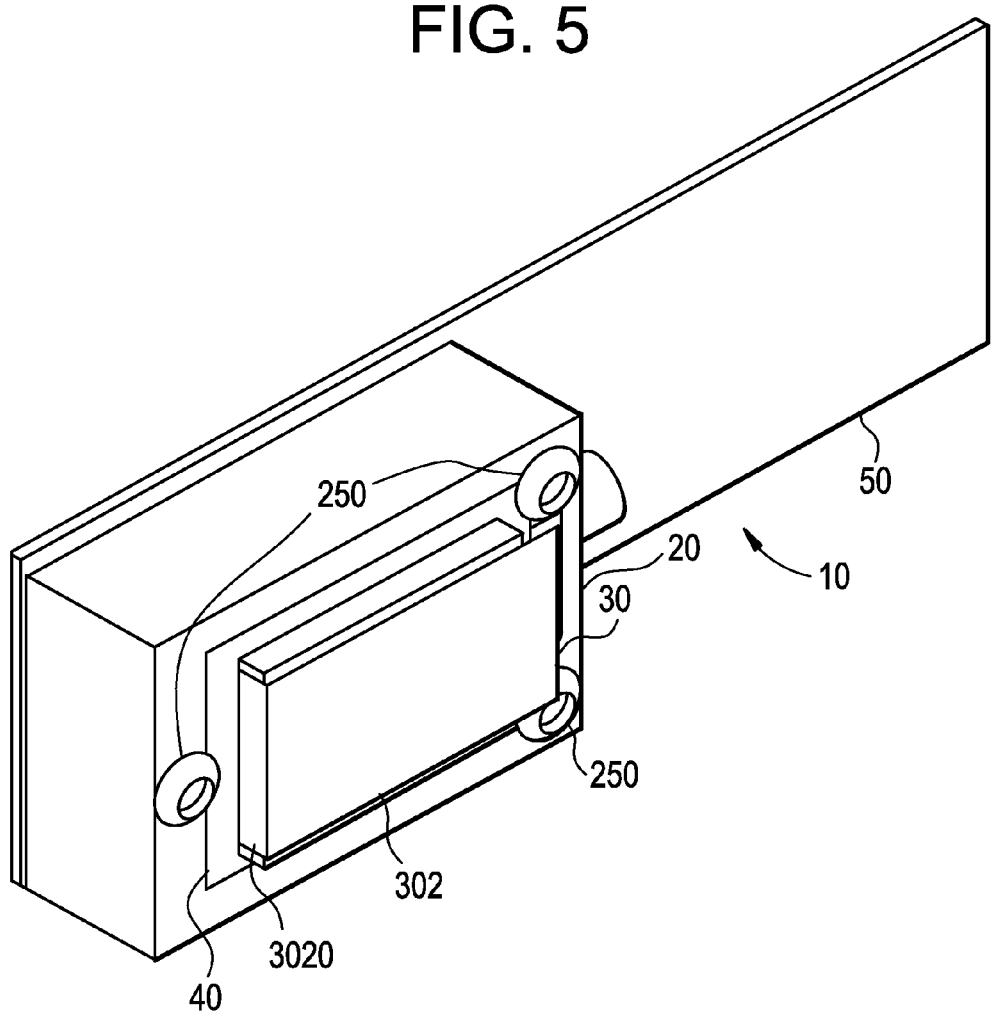
FIG. 5 is a perspective view of the force compensated probe as assembled.

With reference to FIGS. 1, 5 and 8, the copper strips 31, 32 and 301 may be covered by a cover 302 having end portions 3020. The cover 302 may include, for example, insulation material with a silicone based adhesive that serves as a protective cover for the copper strips 31, 32 and 301. The probe 30 and the alternate probe 300 may be utilized with an electronic device that sends alternating current (AC) signals through the copper strips 31, 32 and 301. The cover 302 does not interfere with these AC signals being sent or received as the AC signals are transmittable through the material of the cover 302 and measurements taken with the probe 30 or the alternate probe 300 may be non-direct contact measurements, such as capacitance measurements on thick insulation of generator bars.

Where the cover 302 is employed for the embodiments of FIGS. 1 and 5, the first and second layers 430 and 431 may be discarded.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A force compensated probe for electrical measurement, comprising:
a support structure having a back plate and sidewalls;
a probe for electrical measurement of an article; and
an elastic base disposed to supportively couple the probe to the back plate such that:
the probe normally protrudes away from the back plate beyond distal edges of the sidewalls, and,
when the probe is applied to the article for the electrical measurement such that components of the support structure contact the article, a predefined load is consistently applied to the elastic base irrespective of increases in pressure applied to the probe; and
further comprising:
screw heads arrayed along the sidewalls, protruding away from the back plate, and having respective summits cooperatively establishing a uniform height of the sidewall distal edges from the back plate.

2. The force compensated probe according to claim 1, wherein the back plate and the sidewalls have a substantially rectangular shape.

3. A force compensated probe for electrical measurement, comprising:
an enclosure having a back plate and sidewalls extending around the back plate to form an enclosure defined from the back plate to distal edges of the sidewalls;
a probe for electrical measurement of an article; and
an elastic base disposed within the enclosure to supportively couple the probe to the back plate such that:
the probe normally protrudes away from the back plate beyond the sidewall distal edges, and,
when the enclosure and the probe are applied to the article for the electrical measurement, a predefined load is consistently applied to the elastic base irrespective of increases in pressure applied to the probe; and
further comprising:
screw heads arrayed along the sidewalls, protruding away from the back plate, and having respective summits cooperatively establishing a uniform height of the sidewall distal edges from the back plate.

4. The force compensated probe according to claim 3, further comprising a handle coupled to the enclosure.

5. The force compensated probe according to claim 3, further comprising an electrical connector electrically coupled to the probe via a through-hole defined in one of the sidewalls.

6. The force compensated probe according to claim 3, wherein the back plate and the sidewalls have a substantially rectangular shape.

7. The force compensated probe according to claim 3, wherein the screw heads are arrayed on opposite ends of a first one of the sidewalls and at a mid-point of a second one of the sidewalls, which is opposite the first one of the sidewalls.

8. The force compensated probe according to claim 3, wherein the probe measures electrical impedance of the article.

9. The force compensated probe according to claim 3, wherein the probe comprises copper alloy.

10. The force compensated probe according to claim 3, wherein the probe comprises parallel metallic strips.

11. The force compensated probe according to claim 3, wherein the probe comprises parallel metallic strips having labyrinthine adjacent edges.

12. The force compensated probe according to claim 3, wherein the probe comprises a metallic member surrounding another metallic member.

13. The force compensated probe according to claim 3, wherein the elastic base comprises:
a guide plate; and
elastic elements supportively interposed between the guide plate and the back plate.

14. The force compensated probe according to claim 13, wherein the guide plate comprises a protrusion extendable through a guide slot defined in the back plate to constrain guide plate movement associated with elastic base loading and unloading.

15. The force compensated probe according to claim 13, wherein the elastic elements comprise a plurality of springs arranged such that the guide plate is normally disposed in parallel with the back plate.

16. The force compensated probe according to claim 13, wherein the elastic elements are each anchored to bosses arrayed on the guide plate and are extendable into recesses defined in the back plate.

17. The force compensated probe according to claim 13, wherein the guide plate is formed to define cavities and includes a secondary plate on which portions of the probe are supported for exposure through the cavities.

18. The force compensated probe according to claim 3, further comprising a cover to protectively cover the probe.

19. A force compensated probe for electrical measurement, comprising:

an enclosure having a back plate and sidewalls extending around the back plate to form an enclosure with a depth defined from a plane of the back plate to a plane cooperatively defined by distal edges of the sidewalls;

a protectively covered probe for measurement of electrical impedance of an article; and an elastic base disposed within the enclosure to supportively couple the probe to the back plate such that:

the probe normally protrudes away from the back plate beyond the sidewall distal edges, and, when the enclosure and the probe are applied to the article for the electrical measurement, a combined height of the probe and the elastic base from the plane of the back plate is substantially similar to the enclosure depth with a predefined load thereby consistently applied to the elastic base irrespective of increases in application forces; and further comprising:

screw heads arrayed along the sidewalls, protruding away from the back plate, and having respective summits cooperatively establishing a uniform height of the sidewall distal edges from the back plate.

\* \* \* \* \*